United States Patent [19]

Kizakevich et al.

[11] Patent Number: 4,905,705
[45] Date of Patent: Mar. 6, 1990

[54] IMPEDANCE CARDIOMETER

[75] Inventors: Paul N. Kizakevich, Durham, N.C.; Steve M. Teague, Oklahoma City, Okla.

[73] Assignee: Research Triangle Institute, Research Triangle Park, N.C.

[21] Appl. No.: 318,277

[22] Filed: Mar. 3, 1989

[51] Int. Cl.$^4$ .................................................. A61B 5/04
[52] U.S. Cl. .................................... 128/696; 128/734
[58] Field of Search ................ 128/696, 734, 723, 700

[56] References Cited

U.S. PATENT DOCUMENTS

| | | | |
|---|---|---|---|
| 4,379,460 | 4/1983 | Judell | 128/723 |
| 4,422,458 | 12/1983 | Kravath | 128/696 |
| 4,506,678 | 3/1985 | Russell et al. | 128/723 |
| 4,619,265 | 10/1986 | Morgan et al. | 128/734 |
| 4,781,201 | 11/1988 | Wright et al. | 128/723 |

Primary Examiner—Lee S. Cohen
Assistant Examiner—Scott Getzow
Attorney, Agent, or Firm—Spencer & Frank

[57] ABSTRACT

A heart monitoring system for assessing a patient's cardiac condition. Bioimpedance components induce an electric current through the thorax of a patient's body and a first signal representing amplitude of transthoracic impedance as a function of time is obtained. Electrocardiograph components obtain an electrocardiograph signal from the patient simultaneously with the first signal. First processing circuitry is connected to the bioimpedance components for processing the first signal and producing therefrom a second signal representing cardiovascular hemodynamic changes as a function of time. Second processing circuitry is connected to the electrocardiograph components for measuring changes in the electrocardiograph signal. An analyzer is connected to the first and second processing circuits for producing an output indicating changes in a portion of the second signal over a period of time relative to changes in the electrocardiograph signal over the same period of time. A presentation device presents a visualization of the output of the analyzer for use in providing an assessment of cardiac condition.

18 Claims, 1 Drawing Sheet

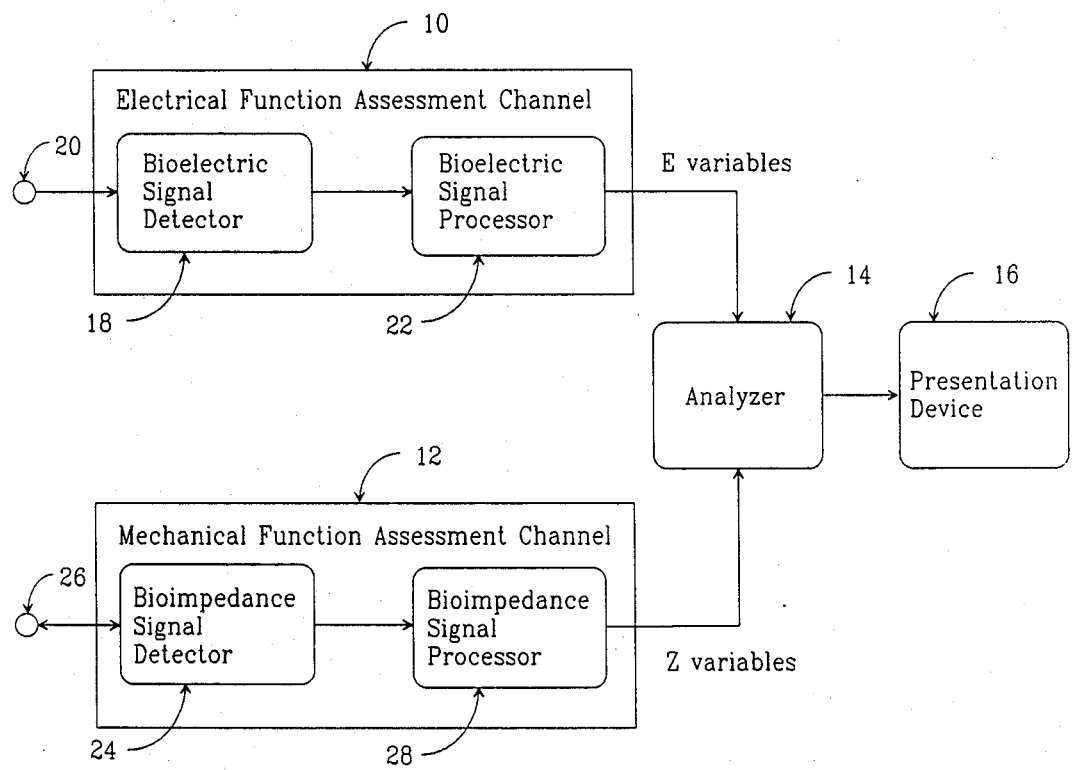

IMPEDANCE CARDIOMETER

BACKGROUND OF THE INVENTION

The field of the invention relates to noninvasive cardiac monitoring, and more particularly to an all electrode-based system employing techniques of impedance cardiography and electrocardiography for measuring mechanical and electrical activity, respectively, of the myocardium for use in the diagnosis of coronary artery disease.

U.S. patent application Ser. No. 07/113,444 filed Oct. 28, 1987, describes a bioelectrical and bioimpedance surveillance system for measuring and analyzing physiological functions through the use of bioelectrical and bioimpedance signals. In the case of cardiac monitoring, the bioelectric signal comprises the electrocardiogram (EKG). As is well known, the EKG detects surface potentials which arise from electrical changes originating within the body, and more specifically from myocardial depolarization and repolarization waves.

Bioimpedance, on the other hand, relates to the electrical impedance of living tissues as measured when electrical energy is applied to the body. Specifically, radio frequency currents are injected into a particular body segment of interest and the potential across this segment is measured from which the bioimpedance signal is obtained. The bioimpedance signal is not of physiological origin, but it can measure physiological phenomena which exhibit varying impedance over a period of time. For monitoring cardiac function by bioimpedance, a low-level electric current is induced across the thorax and changes in the transthoracic impedance during the cardiac cycle are measured. The measured transthoracic signal contains respiratory and cardiac components. However, the cardiac components can be isolated by taking the first derivative of the impedance signal, which essentially filters out the lower frequency respiratory signal. The first derivative of the impedance signal, often referred to as the dZ/dt signal, is related to aortic blood velocity and acceleration as numerous clinical studies reported in the literature have demonstrated.

In the past the focus of those investigating the use of impedance cardiography was to use it to evaluate cardiac function by measuring stroke volume and cardiac output. The theory is based on the principle that because blood is a conductor of electricity, transthoracic electrical impedance changes during the cardiac cycle relate to the amount of blood ejected by the heart. Various empirical formulas have been used to estimate stroke volume from the impedance signal. See, for example, U.S. Pat. No. 4,450,527 to Sramek. The formulas for stroke volume are functions of ventricular ejection time, the electrical resistivity of the blood, distance between the thoracic electrodes, and geometric assumptions about the shape of the thorax. Although the reliability and reproducibility of stroke volume measurements by impedance cardiography have been good in specific instances, in other instances it has not been. In various subsets of patients (for example, in those with hypertension, in exercise studies, and the presence of rapid heartrates), the stroke volume as measured by impedance cardiography has been excessive or inaccurate. Due to such inaccuracies, as well as the use of empirical formulas, and a relative lack of correlation with other presently used noninvasive methods, impedance cardiography has not been widely accepted and is currently viewed primarily as an investigational technique.

The present invention takes a different approach to impedance cardiography. Rather than trying to derive precise quantitative values for parameters such as stroke volume, the methodology of the present invention is to make use of the information provided directly by the impedance cardiogram (dZ/dt). That is, the present inventors have conducted clinical studies which demonstrate that portions of the dZ/dt waveform, and changes thereto over time, directly correlate with cardiac function and dysfunction in much the same way that variations in the electrocardiogram have been correlated with cardiac condition.

The electrocardiogram provides an assessment of electrical function of the myocardium. Clinical studies have established that certain deviations of the electrocardiogram from the norm are suggestive of cardiac dysfunction. For example, it is now widely accepted that myocardial ischemia shows up as an excessive depression in the ST-segment portion of the electrocardiogram. Changes in the electrocardiogram which suggest the presence of ischemia may be misleading, however when unaccompanied by changes in cardiac mechanical function, often referred to as global ventricular performance. Concomitantly, changes in cardiac mechanical function can also occur without accompanying change in electrical activity, so that some episodes of ischemia remain undetected.

Other noninvasive techniques are known for measuring the mechanical function of the heart. For example, nuclear imaging (MUGA) has been used to measure exercise induced changes in ejection fraction. The amount of change, or lack of change in the ejection fraction has been correlated with global ventricular performance. This technique has several drawbacks, not the least of which is that it requires tagging the patient's blood with a radio nuclide, a radioactive material. Additionally, nuclear imaging is capital-intensive so that only large facilities such as hospitals can afford the equipment, and the procedures are costly to the patient. Further, the sensitivity and specificity of exercise-induced ejection fraction changes observed through nuclear imaging are not as high as one would like, presenting an undesirable number of false positives and false negatives.

Doppler echocardiography is another procedure for noninvasively determining global ventricular performance. This technique has been employed in an exercise tolerance test modality with varying success. Its drawbacks are that a skilled person is required to manipulate an ultrasound probe for obtaining appropriate reflections from the aortic bloodflow. This is often difficult, if not impossible, to do through continuous exercise. Usually the patient is required to stop exercising and stop breathing while the probe is manipulated, both of which are considered undesirable for a quality exercise tolerance test. Moreover, the physiques of some patients simply prevent a doppler echocardiogram from being obtained.

Impedance cardiology offers an attractive alternative to doppler echocardiography and MUGA ejection fraction for noninvasively monitoring global ventricular performance. Moreover, because the impedance methodology is electrode-based, it can be combined with electrocardiography for simultaneously obtaining information about both electrical and mechanical activity of the myocardium for assessing cardiac condition and diagnosing coronary artery disease.

SUMMARY OF THE INVENTION

It is an object of the invention to provide a simple and cost-effective methodology for obtaining information about electrical and mechanical activity of the myocardium.

It is a further object of the invention to provide a hybrid discriminator which contains elements of mechanical and electrical activity of the myocardium for assessing the condition of a patient's heart.

It is another object of the invention to combine impedance cardiography and electrocardiography in a single method and apparatus for monitoring a patient's heart for assessing cardiac condition and diagnosing coronary artery disease.

The above and other objects are accomplished according to the invention by the provision of a heart monitoring system for assessing a patient's cardiac condition including: bioimpedance components for inducing an electric current through the thorax of a patient's body and obtaining a first signal representing amplitude of transthorasic impedance as a function of time; electrocardiograph components for obtaining an electrocardiograph signal simultaneously with obtaining the first signal; first processing circuitry connected to the bioimpedance components for processing the first signal and producing therefrom a second signal representing cardiovascular hemodynamic changes as a function of time; second processing circuitry connected to the electrocardiograph components for measuring changes in the electrocardiograph signal; an analyzer connected to the first and second processing circuitry for producing an output indicating changes in a portion of the second signal over a period of time relative to changes in the electrocardiograph signal over the same period of time; and a presentation device connected to the analyzer for visually presenting the output of the analyzer for use in providing an assessment of cardiac condition.

In another aspect of the invention, there is provided a method for diagnosing coronary artery disease in a patient including: measuring transthoracic impedance amplitude as a function of time while the patient is at rest and during exercise; obtaining an electrocardiograph of the patient simultaneously with the measuring step; processing the transthoracic impedance amplitude as a function of time to obtain a signal representing changes in cardiovascular hemodynamics as a function of time; deriving a value for a predetermined parameter obtained from a selected portion of the signal during a cardiac cycle at rest and from a corresponding selected portion of the signal during a cardiac cycle while exercising; forming the difference between the parameter values at rest and during exercise; determining a change in a predetermined aspect of the electrocardiograph between respective ones of the cardiac cycles at rest and during exercise used in the deriving step; and combining the difference in parameter values and the change in the predetermined aspect of the electrocardiograph to form a hybrid indicator for providing as assessment of cardiac condition.

In a specific application, the apparatus and method of the invention are employed in an exercise tolerance test modality whereby the impedance cardiogram and electrocardiogram are obtained from a patient undergoing a specific exercise protocol, such as a Bruce protocol, on an exercise treadmill specially adapted for exercise tolerance testing. The impedance cardiogram and electrocardiogram are taken while the patient is at rest and periodically through various stages of exercise through a maximal exercise stage. Changes in acceleration of aortic bloodflow as reflected by the impedance cardiogram are monitored throughout the exercise protocol. Theoretically, in patients having normal cardiac function, aortic blood acceleration should steadily increase throughout the stages of exercise. In a patient having coronary artery disease, the slope of the trend response of aortic acceleration declines, with the most severely diseased patients, i.e., those having significant stenosis in the left main artery, presenting a relatively flat acceleration trend from rest through maximal exercise.

The electrocardiogram is analyzed for, among other things, changes in ST-segment. ST-segment depression of less than 1 millimeter is considered normal. Exercise-induced ischemia is generally suggested by ST-segment depressions in excess of 1 millimeter. Changes in the slope of the ST-segment have also been correlated with coronary artery disease.

The present invention takes advantages of the information provided by the impedance cardiogram and electrocardiogram by combining, in a specific embodiment, changes in the aortic acceleration and changes in the ST-segment to produce a hybrid diagnostic indicator which has greater sensitivity and specificity than either changes in acceleration or changes in ST-segment have alone during exercise.

In another embodiment of the invention, changes in aortic acceleration are combined with changes in heartrate between rest and a stage of exercise to produce a hybrid discriminator for coronary artery disease. The theory here is, again, in normal patients acceleration will increase along with heartrate from rest through various stages of exercise. In diseased patients, the acceleration will increase at a slower rate or possibly remain flat, and the heartrate will increase, possibly at a faster rate, to accommodate the normal need for additional oxygen and to compensate for the lack of aortic acceleration. By forming a ratio of the change in aortic acceleration and the change in heartrate through stages of exercise, one can see that the trend response of this ratio will be significantly different for normal patients as opposed to patients having coronary artery disease.

BRIEF DESCRIPTION OF THE DRAWINGS

The sole FIGURE in the drawings is a block circuit diagram of a cardiometer in accordance with the invention.

PREFERRED EMBODIMENT OF THE INVENTION

Referring to the FIGURE, there is illustrated an impedance cardiometer according to the invention including an electrical function assessment channel 10 and a mechanical function assessment channel 12, each being connected to an analyzer 14. The output of the analyzer is connected to a presentation device 16, such as a computer monitor and/or printer.

The electrical function assessment channel 10 includes a bioelectrical signal detector 18 for detecting the electrocardiograph signal received from a standard electrocardiograph electrode lead set (not shown) connected to a single or multi-channel input 20. The electrocardiograph signal is passed to a bioelectric signal processor 22 where the electrocardiograph signal may be averaged over a number of cardiac cycles to eliminate motion artifacts according to techniques known in the art, and to measure desired parameters such as ST-segment depression amplitude and/or slope, heartrate, and other electrocardiogram parameters of interest, which will be collectively referred to as E variables, as shown in the drawing. The E variables are fed to analyzer 14. The components in the electrical function assessment channel 10 are commercially available from a variety of suppliers and do not, per se, comprise the present invention.

Mechanical function assessment channel 12 includes a bioimpedance signal detector 24 which receives an input at input terminal 26 from bioimpedance electrodes (not shown) connected at the neck and at the thorax just below the xyphoid process of the patient. The output of the bioimpedance signal detector is the transthoracic impedance signal amplitude as a function of time. The impedance signal, which contains both respiratory and cardiac components, is fed to bioimpedance signal processor 28 where the first derivative is taken to eliminate the respiratory component as is well known in the art. Bioimpedance signal processor 28 also averages the dZ/dt signal over several cardiac cycles to eliminate motion artifacts and other noise, and measures various variables including the acceleration of the impedance signal and other parameters of interest which will be collectively referred to as the Z variables, as shown in the drawing. Preferably, the acceleration signal is an average acceleration derived by dividing the peak velocity by the rise time of the systole portion of the impedance cardiogram. If the peak acceleration is desired, it may be derived by taking the second derivative of the impedance signal and measuring the maximum amplitude of the $d^2Z/d^2t$ signal. The hardware components and software for implementing mechanical function assessment channel 12 are described in greater detail in U.S. patent application Ser. No. 07/113,444 filed Oct. 18, 1987 to Kizakevich et al, the disclosure of which is hereby incorporated by reference.

Analyzer 14 continuously computes the change in ST-segment depression from a nominal value, such as at rest, and similarly computes the change in aortic acceleration over time from the nominal value at rest. Analyzer 14 also combines the change in aortic acceleration and the change in ST-segment depression by preferably taking the ratio of these two values. Clinical studies have demonstrated that this ratio comprises a good diagnostic discriminator for coronary artery disease. In fact, the studies have shown a synergistic result, in that the ratio provides a better diagnostic discriminator for coronary artery disease than either acceleration or ST-segment depression considered alone during exercise tolerance testing.

The ratio of the change in the aortic acceleration over the change in ST-segment depression is fed to the presentation device which may comprise a video display or a printer for providing a visual presentation of the trend response over time of the aforementioned ratio. Preferably, the electrocardiogram and impedance cardiogram will also be fed directly to the presentation device and displayed and/or printed in time sequence with the trend response of the ratio.

In another embodiment of the invention, change of heartrate over time could be used in place of change in ST-segment depression in calculating the diagnostic ratio.

In yet still a further embodiment of the invention, instead of combining impedance and electrical variables as a ratio, a linear combination of impedance and electric variables, including but not limited to, aortic acceleration, ST-segment depression, ST-segment slope, and/or heartrate could be combined with appropriate constants to form a hybrid diagnostic indicator for coronary artery disease.

Analyzer 14 is preferably implemented in the form of a personal computer, such as an IBM AT, and appropriately configured software for accomplishing the relatively straightforward arithmetic computations described above.

The impedance cardiometer according to the invention may, with suitable miniterization of circuitry, also be used as an ambulatory monitor in much the same way as a Holter monitor for long-term monitoring of mechanical and electrical activity of a person's heart. It also has application for bedside monitoring in intensive care environments.

Although the invention is described with reference to a specific preferred embodiment, modifications within the scope of the invention may be apparent to those skilled in the art. Therefore, the true scope of the invention is understood to be determined by the appended claims.

What is claimed is:

1. A heart monitoring system for assessing a patient's cardiac condition comprising:
   bioimpedance means for inducing an electric current through the thorax of a patient's body and obtaining a first signal representing amplitude of transthoracic impedance as a function of time;
   electrocardiograph means for obtaining an electrocardiograph signal from the patient simultaneously with obtaining the first signal;
   first processing means connected to said bioimpedance means for processing the first signal and producing therefrom a second signal representing cardiovascular hemodynamic changes as a function of time;
   second processing means connected to said electrocardiograph means for measuring changes in the electrocardiograph signal;
   analysis means connected to said first and second processing means for producing an output indicating changes in a portion of the second signal over a period of time relative to changes in the electrocardiograph signal over the same period of time; and
   presentation means connected to said analysis means for visually presenting the output of said analysis means for use in providing an assessment of cardiac condition.

2. The system of claim 1, wherein said second processing means includes an ST-segment measuring means for measuring changes in the ST-segment of the electrocardiograph signal.

3. The system of claim 2, wherein said first processing means includes means for producing an acceleration signal indicating aortic blood acceleration and said analysis means includes means for indicating changes in the acceleration signal over a period of time relative to changes in the ST-segment of the electrocardiograph signal over the same period of time.

4. The system of claim 3, wherein said analysis means includes combining means for combining changes in the acceleration signal with changes in the ST-segment of the electrocardiograph signal over the same period of time to produce a parameter having cardiac diagnostic sensitivity.

5. The system of claim 4, wherein said combining means forms a ratio between a change in amplitude of the acceleration signal and a change in the ST-segment of the electrocardiograph signal over the same period of time.

6. The system of claim 5, wherein the change in ST-segment portion of the electrocardiograph signal comprises a change in ST-segment amplitude.

7. The system of claim 1, wherein said second processing means includes a heartrate measuring means for measuring changes in heart rate as a function of time.

8. The system of claim 7, wherein said first processing means includes means for producing an acceleration signal indicating aortic blood acceleration and said analysis means includes means for indicating changes in the acceleration signal over a period of time relative to changes in heartrate over the same period of time.

9. The system of claim 8, wherein said analysis means includes combining means for combining changes in amplitude of the acceleration signal with changes in heartrate over the same period of time to produce a parameter having cardiac diagnostic sensitivity.

10. The system of claim 9, wherein said combining means forms a ratio between a change in the acceleration signal amplitude and a change in heartrate.

11. A method for diagnosing coronary artery disease in a patient comprising:
measuring transthoracic impedance amplitude as a function of time while a patient is at rest and during exercise;
obtaining an electrocardiograph of the patient simultaneously with said measuring step;
processing the transthoracic impedance amplitude as a function of time to obtain a signal representing changes in cardiovascular hemodynamics as a function of time;
deriving a value for a predetermined parameter obtained from a selected portion of the signal during a cardiac cycle at rest and from a corresponding selected portion of the signal during a cardiac cycle while exercising;
forming the difference between the parameter values at rest and during exercise;
determining a change in a predetermined aspect of the electrocardiograph between respective ones of the cardiac cycles at rest and during exercise used in said deriving step; and
combining the difference in parameter values and the change in the predetermined aspect of the electrocardiograph to form a hybrid indicator for providing an assessment of cardiac condition.

12. The method of claim 11, wherein said determining step includes determining a change in the ST-segment of the electrocardiograph between the respective ones of the cardiac cycles at rest and during exercise.

13. The method of claim 12 wherein said deriving step includes deriving values for aortic blood acceleration at rest and during exercise, and said forming and combining steps include using values of aortic acceleration as the parameter values.

14. The method of claim 13, wherein said determining step includes determining a change in ST-segment amplitude.

15. The method of claim 14, wherein said combining step includes forming a ratio between (a) the difference in values for blood acceleration at rest and during exercise, and (b) the change in ST-segment amplitude between rest and exercise.

16. The method of claim 11, wherein said determining step includes determining a change in heartrate between the respective ones of the cardiac cycles at rest and during exercise.

17. The method of claim 16, wherein said deriving step includes deriving values for aortic blood acceleration at rest and during exercise, and said forming and combining steps include using values of aortic acceleration as the parameter values.

18. The method of claim 17, wherein said combining step includes forming a ratio between (a) the difference in values for aortic blood acceleration at rest and during exercise, and (b) the change in heartrate between rest and exercise.

* * * * *